United States Patent [19]

Brodsky et al.

[11] Patent Number: 5,355,876
[45] Date of Patent: Oct. 18, 1994

[54] PATIENT VENTILATING APPARATUS WITH MODULAR COMPONENTS

[75] Inventors: David L. Brodsky, Providence; Harry O. Olsen, Warwick, both of R.I.

[73] Assignee: Superior Healthcare Group, Inc., Cumberland, R.I.

[21] Appl. No.: 878,968

[22] Filed: May 6, 1992

[51] Int. Cl.$^5$ .............................. A61M 16/00
[52] U.S. Cl. .................... 128/202.27; 128/207.14; 128/912
[58] Field of Search ............ 128/202.27, 911, 912, 128/909, 207.14; 285/921, 332, 332.1

[56] References Cited

U.S. PATENT DOCUMENTS

| | | | |
|---|---|---|---|
| 3,215,141 | 11/1965 | Podhora | 604/163 |
| 3,335,723 | 8/1967 | Waldman, Jr. | 604/163 |
| 3,388,705 | 6/1968 | Grosshandler | 128/912 X |
| 3,825,001 | 7/1974 | Bennet et al. | 604/170 |
| 3,902,500 | 9/1975 | Dryden | 128/207.14 |
| 3,991,762 | 11/1976 | Radford | 604/119 |
| 4,068,659 | 1/1978 | Moorehead | 604/53 |
| 4,326,520 | 8/1982 | Alley | 604/171 |
| 4,327,723 | 5/1982 | Frankhouser | 604/171 |
| 4,327,735 | 5/1982 | Hampson | 604/171 |
| 4,392,853 | 7/1983 | Muto | 604/171 |
| 4,506,665 | 3/1985 | Andrews | 128/202.27 |
| 4,510,933 | 4/1985 | Wendt | 128/207.14 |
| 4,551,137 | 11/1985 | Osborne | 604/171 |
| 4,552,142 | 11/1985 | Hoffman | 128/207.16 |
| 4,563,176 | 1/1986 | Gustavsson et al. | 604/163 |
| 4,613,329 | 9/1986 | Bodicky | 604/158 |
| 4,622,033 | 11/1986 | Taniguchi | 604/172 |
| 4,634,433 | 1/1987 | Osborne | 604/171 |
| 4,696,296 | 9/1987 | Palmer | 128/207.16 |
| 4,767,409 | 8/1988 | Brooks | 604/171 |
| 4,834,726 | 5/1989 | Lambert | 604/281 |
| 4,838,255 | 6/1989 | Lambert | 128/202.16 |
| 4,846,167 | 7/1989 | Tibbals | 128/202.27 |
| 5,083,561 | 1/1992 | Russo | 128/207.16 |
| 5,088,486 | 2/1992 | Jinotti | 128/207.14 |

FOREIGN PATENT DOCUMENTS 1621945 1/1991 U.S.S.R. ............ 128/202.27

Primary Examiner—Edgar S. Burr
Assistant Examiner—Eric P. Raciti
Attorney, Agent, or Firm—Samuels, Gauthier & Stevens

[57] ABSTRACT

An apparatus for ventilating and aspirating the respiratory system of a tracheostomy patient includes a patient module connectable to a supply of air and to the trachea of a patient, a center module including a first end element connected to the patient module, a second end element, a tubular catheter element extending slidably and sealingly through the first end element, a flexible tubular plastic sleeve extending between the first and second end elements around the catheter element, and a vacuum module connected to the second end element of the center module and connectable to a vacuum source for applying vacuum to the catheter element. The first and second end elements of the center module are releasably connected to the patient module and the vacuum module, respectively, so that the center module, including the catheter element, can be readily replaced without replacing the patient module and/or the vacuum module.

3 Claims, 2 Drawing Sheets

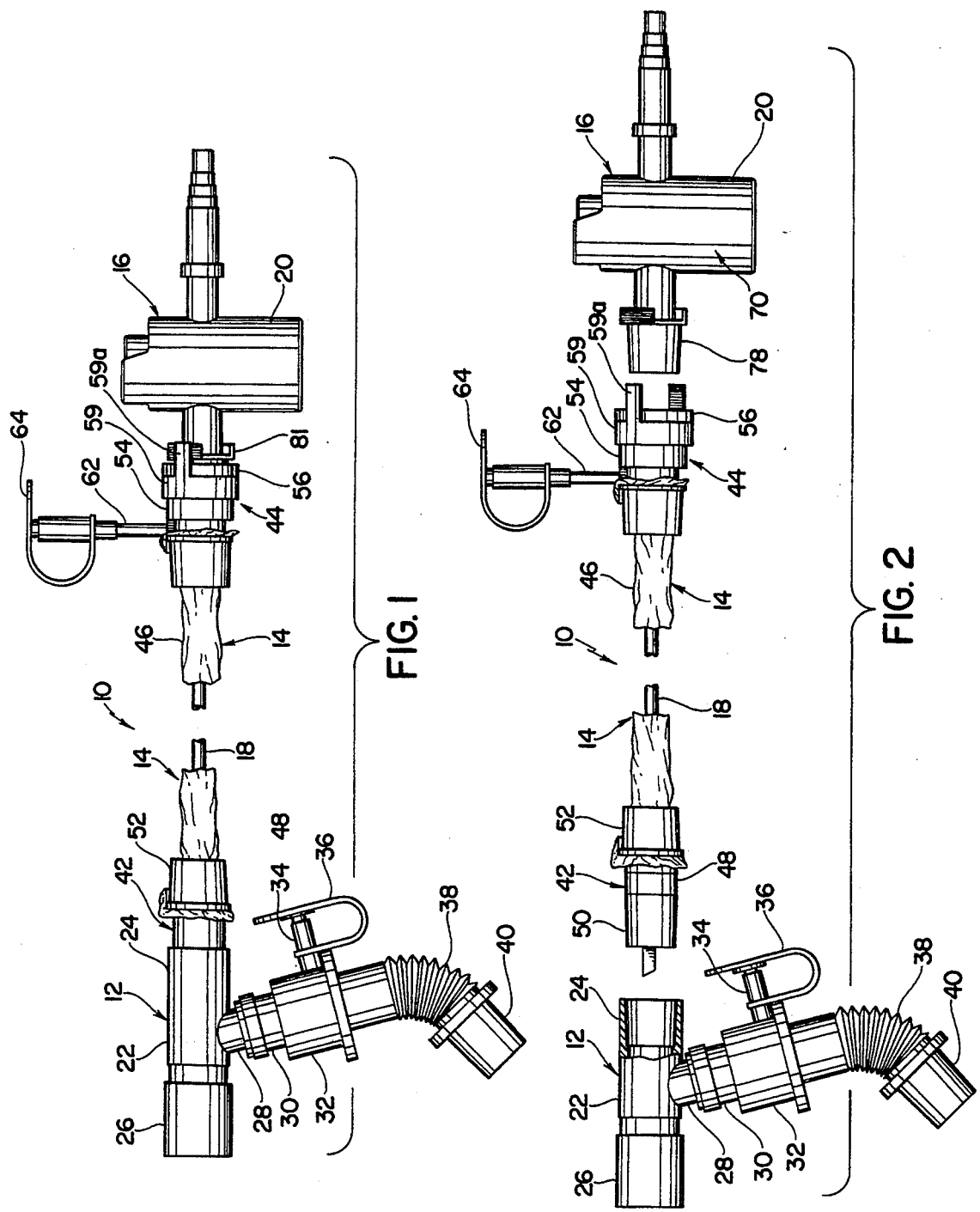

PATIENT VENTILATING APPARATUS WITH MODULAR COMPONENTS

The instant invention relates to medical apparatus and more particularly to a patient ventilating apparatus for ventilating and aspirating the respiratory system of a patient.

A number of different types of apparatus have been heretofore available for ventilating tracheostomy patients and for aspirating fluids, such as mucous, from the trachea of such patients during ventilation. Most of the heretofore available devices of this general type have comprised connector fittings which are adapted to be connected to tracheostomy connectors installed in the trachea of patients and also to air supplies for involuntarily supplying air to and withdrawing air from the lungs of patients. Devices of this type have further comprised aspirating catheters which are adapted to be connected to vacuum sources for aspirating fluids from the trachea of patients. These devices have still further comprised control means for controlling the levels of vacuum applied to the aspirating catheters thereof. The aspirating catheters of devices of this type have generally been slidably but sealingly received in the connector fittings thereof so that they can be longitudinally advanced into and withdrawn from the trachea of patients. Devices of this type have still further generally comprised tubular collapsible outer sleeves which extend around the catheter elements thereof, and between the connector fittings thereof and the vacuum control elements thereof so that the catheter elements can be manipulated by attending physicians or technicians without requiring the hands of the physicians or technicians to come into direct contact with the catheter elements.

Devices of the above type, which represent the closest prior art of the subject invention of which the applicant is aware, are disclosed in the U.S. patents to Podhora U.S. Pat. No. 3,215,141; Waldman, Jr. U.S. Pat. No. 3,335,723; Bennet et al U.S. Pat. No. 3,825,001; Dryden U.S. Pat. No. 3,902,500; Radford U.S. Pat. No. 3,991,762; Moorehead U.S. Pat. No. 4,068,659; Alley U.S. Pat. No. 4,326, 520; Frankhouser U.S. Pat. No. 4,327,723; Hampson U.S. Pat. No. 4,327,735; Muto U.S. Pat. No. 4,392,853; Osborne U.S. Pat. No. 4,551,137; Gustavsson et al U.S. Pat. No. 4,563,176; Bodicky U.S. Pat. No. 4,613,329; Taniguchi U.S. Pat. No. 4,622,033; Osborne U.S. Pat. No. 4,634,433; Palmer U.S. Pat. No. 4,696, 296; Brooks U.S. Pat. No. 4,767,409; Lambert U.S. Pat. No. 4,834,726; Russo U.S. Pat. No. 5,083,561, and the applicant's co-pending application Ser. No. 07/737,422. However, while these references disclose a wide variety of patient ventilating apparatus, including some which have detachable patient modules, they fail to disclose or suggest a patient ventilating apparatus having a replaceable center module or catheter section. Hence, the above references are believed to be of only general interest with respect to the subject invention.

It has been found that one of the main problems with the heretofore available ventilating apparatus has been the overall cost thereof. Further, it has been found that this disadvantage has been magnified by the fact that it has generally been necessary to frequently replace the heretofore available apparatus (in many cases, daily or every other day). Hence, there is a recognized need for an effective patient ventilating apparatus which is adapted to reduce the overall cost associated with ventilating a patient over a long period of time.

The instant invention provides an effective apparatus for ventilating and aspirating the respiratory system of a patient over a prolonged period of time at a significantly reduced cost. Specifically, the apparatus of the subject invention comprises removably connected patient, center, and vacuum modules to enable the center module to be quickly and easily replaced without replacing the patient module and/or the vacuum module, so that the cost of providing an effective, clean, and operative ventilating apparatus for a patient over a prolonged period of time can be substantially reduced. Still more specifically, the apparatus of the subject invention comprises a patient module which includes a tubular connector which is connectable to a supply of air and to the trachea of a patient for involuntarily supplying air to and withdrawing air from the lungs of the patient. The apparatus further comprises a center module including a first end element which is releasably connected to the patient module, a second end element, an elongated flexible tubular catheter element which is connected to the second end element and extends slidably and sealingly through the first end element, and an elongated collapsible tubular plastic sleeve which extends between the first and second end elements around the catheter element. The apparatus still further comprises a vacuum module which is releasably connected to the second end element and adapted to be connected to a source of vacuum for applying vacuum to the lumen in the catheter element. The vacuum module further includes a control member for controlling the application of vacuum to the catheter element. The patient module and the center module are preferably releasably connected by means of tapered male and female friction fit connector elements which are releasably receivable in frictional engagement for securing the patient module to the center module, and the center module is preferably releasably connected to the vacuum module in a similar manner.

Accordingly, it is a primary object of the instant invention to provide an effective apparatus for aspirating the respiratory system of a patient comprising releasably connected patient center and vacuum modules.

Another object of the instant invention is to provide an effective ventilating apparatus for ventilating the respiratory system of a patient comprising a readily replaceable center catheter element module.

An even still further object of the instant invention is to provide an effective apparatus for ventilating the respiratory system of a patient over a prolonged period of time with a reduced overall equipment cost.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention:

FIG. 1 is a side elevational view of the apparatus of the subject invention with the patient center and vacuum modules in assembled relation;

FIG. 2 is a similar view with the patient center and vacuum modules in disassembled relation.

DESCRIPTION OF THE INVENTION

Figure 3:
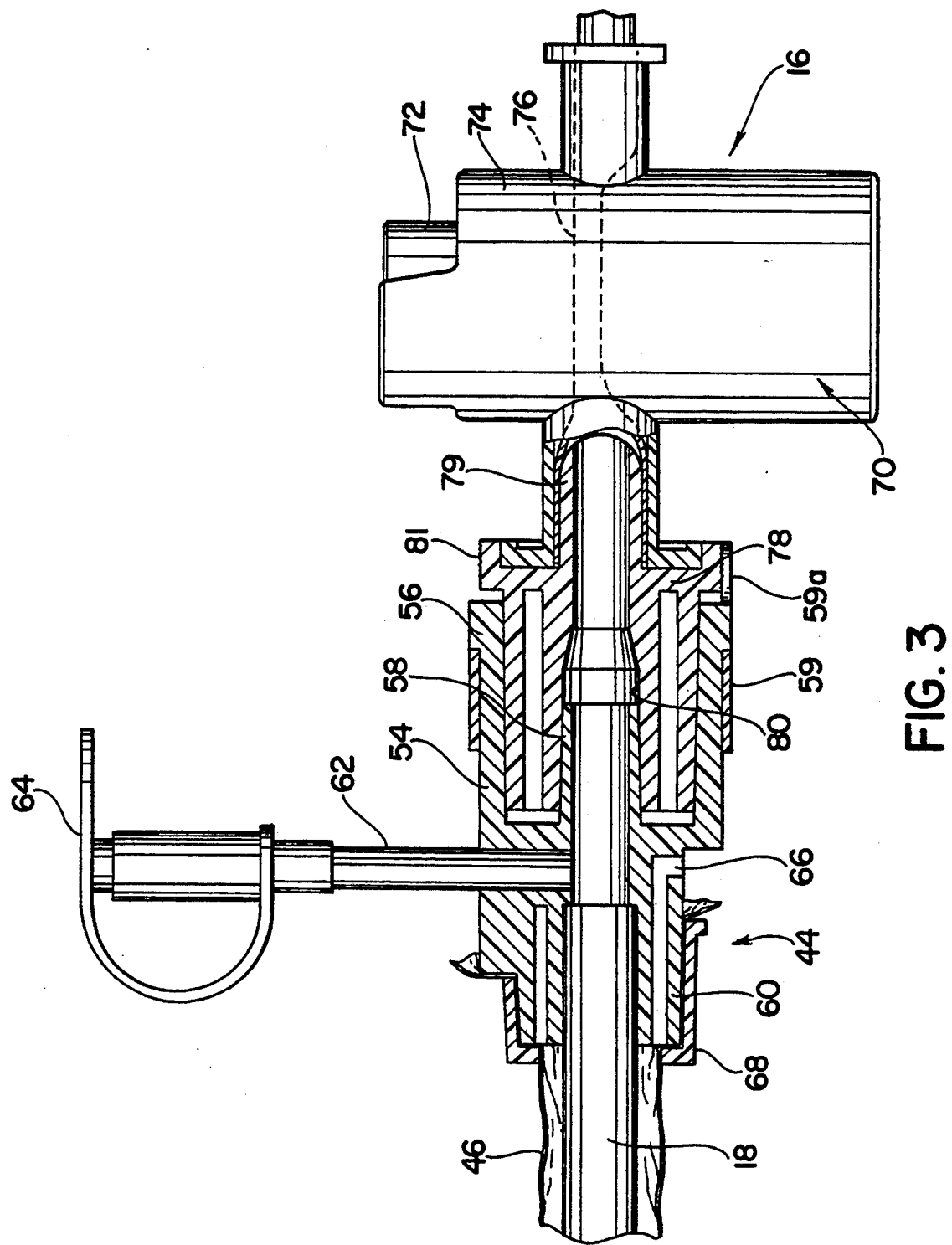
FIG. 3 is an enlarged sectional view of detachable connection between the center module and the vacuum module.

Referring now to the drawings, the patient ventilating apparatus of the instant invention is illustrated and generally indicated at 10 in FIGS. 1 and 2. The apparatus 10 comprises a patient module generally indicated at 12, a center module generally indicated at 14, and a vacuum module generally indicated at 16. The patient module 12 is adapted to be connected to a tracheostomy connector installed in the trachea of a patient for involuntarily supplying air to and withdrawing air from the lungs of the patient. The center module 14 is removably connected to the patient module 12, and it includes a center catheter element 18 which is advanceable through the patient module 12 for aspirating fluids from the trachea of the patient. The vacuum module 16 is releasably connected to the center module 14, and it is adapted to be connected to a suitable source of vacuum. The vacuum module 16 includes a control member 20 for controlling the application of vacuum to the catheter element 18 once the vacuum module 16 is connected to a vacuum source. In any event, because the center module 14 is releasably connected to both the patient module 12 and the vacuum module 16, the center module 14 can be removed and replaced without replacing the patient module 12 and/or the vacuum module 16.

The patient module 12 comprises a tubular main portion 22 having a tapered female friction fit connector 24 at one end thereof, and a swivel element 26 which is rotatably secured to the main section 22 at the opposite end thereof. The patient module 12 further comprises an elbow section 28 which extends angularly outwardly from the main section 22 at one side thereof, a swivel section 30 which is rotatably secured to the elbow section 28, an enlarged section 32 having a sampling port 34 thereon, a closure cap 36 on the sampling port 34, a flexible section 38, and a tapered male friction fit connector 40 on the end of the flexible section 38. The swivel element 26 of the patient module 12 is adapted to be connected to a tracheal connector element which is pre-installed in a patient, and the tapered male connector fitting 40 is adapted to be connected to a source of air for ventilating the patient in a conventional manner.

The center section 14 comprises a first end assembly generally indicated at 42, a second end assembly generally indicated at 44, a catheter element 18, and a tubular flexible plastic sleeve 46 which extends between the end assemblies 42 and 44 around the catheter element 18. The first end assembly 42 comprises a main section 48 having a tapered male friction fit connector element 50 thereon. The first end assembly 42 further comprises an internal ring-like elastomeric seal element (not shown) in the interior of the main section 48 for slidably yet sealingly engaging the catheter element 18 so that the catheter element 18 is advanceable and retractable in sealed engagement through the first end assembly 42 in a conventional manner. Also included in the first end assembly 42 is a retaining collar 52 which extends over the adjacent end of the flexible plastic sleeve 46 and is secured to the main section 48, such as by an adhesive or ultrasonic welding, in order to sealingly secure the adjacent end of the sleeve 46 to the first end assembly 42. The second end assembly 44 comprises a main section 54 having a tapered female friction fit connector element 56 formed therein, and an interior tubular section 58 which is formed in concentric inwardly spaced relation to the connector element 56. A locking ring 59 including a pair of locking arms 59a is rotatably received on the connector element 56, the locking arms 59a having inwardly facing ridges thereon which are engageable with corresponding components on the vacuum module 16 for releasably locking the center module 14 thereto. A male end element 60 is formed at the opposite end of the main section 54 from the female connector element 56, and the terminal end of the catheter element 18 is received and secured in the male connector 60, so that the catheter element 18 communicates with the interior of the tubular section 58. Also provided on the second end assembly 44 is an irrigation port 62 which communicates with the interior lumen in the catheter element 18, the irrigation port 62 having a closure member 64. A vent 66 is also formed in the main portion 54 for venting air from the interior of the collapsible sleeve 46. The adjacent end of the sleeve 46 is received over the male fitting 60, and a collar 68 is received over the sleeve 46 and the male fitting 60 and secured thereto by suitable means, such as ultrasonic welding or an adhesive, in order to permanently secure the adjacent end of the sleeve 46 to the second end assembly 44.

The vacuum module 16 comprises a clamp assembly generally indicated at 70 which is generally similar to the clamp assembly disclosed in the applicant's copending U.S. application Ser. No. 07/737,422, including a button portion 72 and a housing 74. The vacuum assembly 16 further comprises a collapsible tubular member 76 which extends through the clamp assembly 70 and a tapered male friction fit connector element 78. The clamp assembly 70 is adapted so that it normally retains the tubular element 76 in a collapsed disposition, although, it is operable by depressing the button portion 72 relative to the housing 74, for releasing the tubular element 76 so that the latter is resiliently returned to a non-collapsed disposition. The tapered male friction fit connector element 78 includes a reduced tubular end portion 79 which is received in a tubular section of the housing 74. The tubular element 76 is received on the reduced tubular end portion 79 in the housing 74, and the connector element 78 is secured to the housing 74, as illustrated. The tapered male friction fit connector element 78 has an inner cavity 80 formed thereon and it includes a pair of spaced outer surface segments 81 having ridges thereon which are engageable by the locking arms 59a for releasably locking the center module 14 and the vacuum module 16 together. A conventional tapered connector element 82 is received in the tubular element 76 at the opposite end of the clamp 70 for connecting the tubular element 76 to a suitable vacuum source.

For use and operation of apparatus 10 the patient module 12 is connected to a tracheal connector installed in the trachea of a patient, and the connector 40 is connected to a suitable source of air for ventilating the lungs of the patient. The vacuum module 16 is attached to a suitable vacuum source, and the center module 10 is assembled with the patient module 12 and the vacuum module 16. Specifically, the tapered male connector 50 is assembled in the tapered female connector 24, and the tapered male connector 78 is assembled in the tapered female connector 56, so that the locking arms 59a engage the ridges on the surface segments 81. The catheter element 18 can then be manipulated through the sleeve 46, so that it is advanced into the trachea of the patient in order to aspirate fluids therefrom.

It has been found that during normal use the aspirating catheter element 18 tends to build up residual substances, such as dried mucous, etc., on both the interior and exterior surfaces thereof when the catheter element 18 is repeatedly utilized over the course of a day or two. Therefore, it frequently becomes necessary to replace the catheter element 18. While with most patient ventilating apparatus it is necessary to replace the entire apparatus when the catheter element thereof becomes contaminated with residues, the apparatus 10 is specifically constructed so that it is possible to replace only the center module 14 rather than replacing the entire apparatus 10. Accordingly, it is not necessary to incur the added expense of replacing the patient module 12 and the vacuum module 16 each time the center module 14, which includes the catheter element 18, is replaced.

It is seen therefore that the instant invention provides an effective apparatus for ventilating the respiratory system of a patient. The apparatus 10 can be effectively utilized for ventilating the respiratory system of a patient, and the catheter element 18 can be utilized for aspirating fluids from the trachea of the patient. Further, when the catheter element 18 becomes contaminated it is possible to replace the center module 14 without also replacing the patient module 12 and the vacuum module 16. Hence, in many instances it is not necessary to go to the expense of replacing the entire apparatus 10. Accordingly, it is seen that the apparatus 10 of the instant invention represents a significant advancement in the art relating to patient ventilating apparatus which has substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed:

1. In an apparatus for ventilating and aspirating the respiratory system of a patient, said apparatus comprising: a patient module including tubular connecting means connectable to a supply of air and to the trachea of the patient for involuntarily supplying air to and withdrawing air from the lungs of the patient; a center module including a first end element connected to said patient module, a second end element, an elongated flexible tubular catheter element permanently connected to said second end element and extending slidably and sealingly through said first end element, and an elongated, collapsible, tubular plastic sleeve connected to said first and second end elements and extending therebetween around said catheter element; and a vacuum module connected to said second end element and adapted to be connected to a source of vacuum for applying vacuum to said catheter element, said vacuum module including means for controlling the application of vacuum to said catheter element, said first end element being releasably connected to said patient module and said second end element being releasably connected to said vacuum module and including first interconnecting means for releasably interconnecting said sleeve to said vacuum module and second interconnecting means for simultaneously, releasably, sealingly interconnecting said catheter element to said vacuum module to permit removal and replacement of said center module as a single unit without replacing said patient module or said vacuum module, said first and second interconnecting means comprising concentric tubular male and female extensions on said sleeve and on said vacuum module arranged to coact in a friction fit respectively with one another.

2. In the apparatus of claim 1, one of said patient module and said first end element including a tapered male friction-fit connector element, the other one of said patient module and said first end element including a tapered female friction-fit connector element, said tapered male friction-fit connector element being releasably receivable in frictional engagement in said tapered female friction-fit connector element for releasably securing said patient module to said center module.

3. In the apparatus of claim 1, said first and second interconnecting means being integrally formed in a unitized construction.

* * * * *